United States Patent
Ralph et al.

(10) Patent No.: US 7,048,763 B2
(45) Date of Patent: *May 23, 2006

(54) INTERVERTEBRAL SPACER DEVICE HAVING A RADIALLY THINNING BELLEVILLE SPRING

(75) Inventors: James D. Ralph, Seaside Park, NJ (US); Stephen Tatar, Montville, NJ (US)

(73) Assignee: SpineCore, Inc., Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/783,292

(22) Filed: Feb. 18, 2004

(65) Prior Publication Data

US 2004/0167627 A1 Aug. 26, 2004

Related U.S. Application Data

(63) Continuation of application No. 09/968,047, filed on Oct. 1, 2001, now abandoned.

(51) Int. Cl.
*A61F 2/44* (2006.01)

(52) U.S. Cl. .............................. 623/17.13; 623/17.15; 623/17.14

(58) Field of Classification Search ............. 623/17.13, 623/17.14, 17.15; 606/61
See application file for complete search history.

(56) References Cited

U.S. PATENT DOCUMENTS 5,893,889 A * 4/1999 Harrington ................ 623/17.16
5,989,291 A * 11/1999 Ralph et al. ............. 623/17.15

* cited by examiner

*Primary Examiner*—Brian E Pellegrino
(74) *Attorney, Agent, or Firm*—Lerner, David, Littenberg, Krumholz & Mentlik, LLP (57) ABSTRACT

An intervertebral spacer device having a pair of opposing plates for seating against opposing vertebral bone surfaces, separated by a subassembly including a ball captured in a curvate volume, at least a portion of the curvate volume being formed in a convex element that is maintained against a first plate by a retaining wall and a retaining ring.

9 Claims, 5 Drawing Sheets

INTERVERTEBRAL SPACER DEVICE HAVING A RADIALLY THINNING BELLEVILLE SPRING

CROSS-REFERENCE TO RELATED APPLICATION

This application is a continuation application of U.S. patent application Ser. No. 09/968,047 filed Oct. 1, 2001 now abandoned entitled "An Intervertebral Spacer Device Having a Radially Thinning Belleville Spring", which is fully incorporated by reference herein.

FIELD OF THE INVENTION

This invention relates generally to a spinal implant assembly for implantation into the intervertebral space between adjacent vertebral bones to simultaneously provide stabilization and continued flexibility and proper anatomical motion, and more specifically to such a device which utilizes a belleville washer having a radially varying thickness profile as a restoring force generating element.

BACKGROUND OF THE INVENTION

The bones and connective tissue of an adult human spinal column consists of more than 20 discrete bones coupled sequentially to one another by a tri-joint complex which consists of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column of bones is highly complex in that it includes over twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes which can result in spinal pathologies for which surgical intervention may be necessary. A variety of systems have been disclosed in the art which achieve immobilization and/or fusion of adjacent bones by implanting artificial assemblies in or on the spinal column. The region of the back which needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Figure 1:
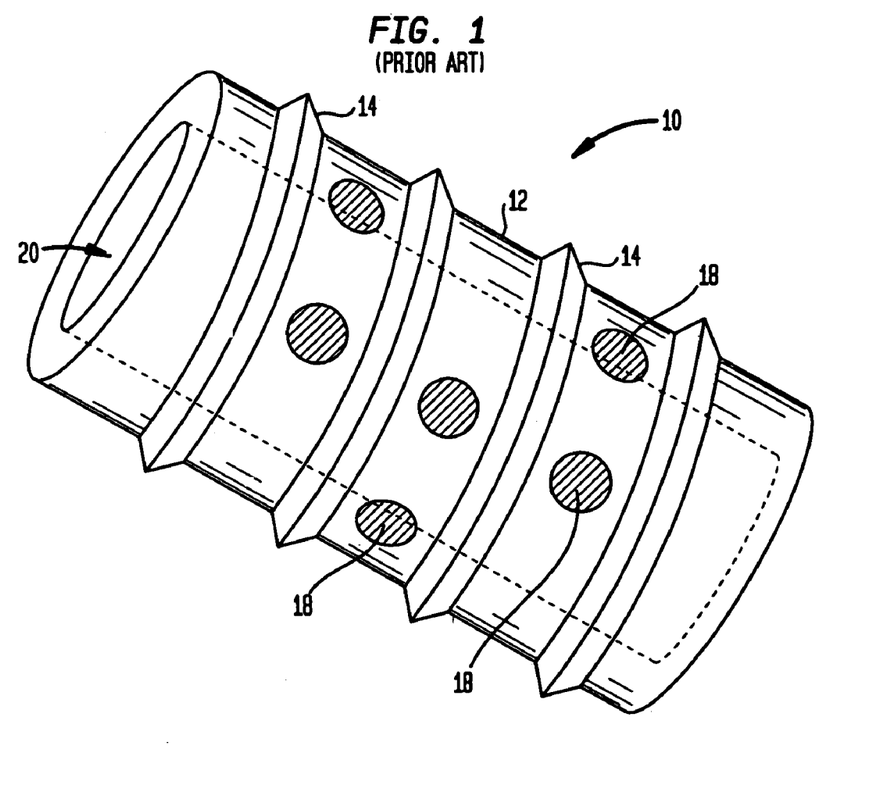
FIG. 1 is a side perspective view of an interbody fusion device of the prior art.
Figure 2:
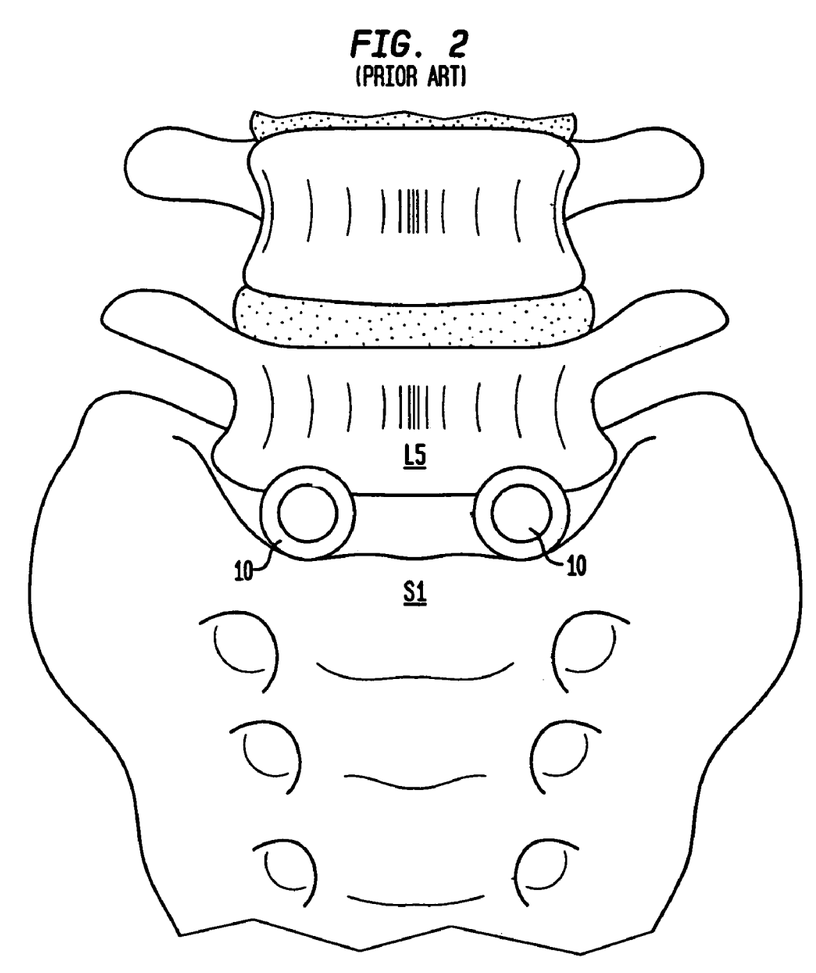
FIG. 2 is a front view of the anterior portion of the lumbo-sacral region of a human spine, into which a pair of interbody fusion devices of the type shown in FIG. 1 have been implanted.

Referring now to FIGS. 1 and 2, in which a side perspective view of an intervertebral body cage and an anterior perspective view of a post implantation spinal column are shown, respectively, a more complete description of these devices of the prior art is herein provided. These cages 10 generally comprise tubular metal body 12 having an external surface threading 14. They are inserted transverse to the axis of the spine 16, into preformed cylindrical holes at the junction of adjacent vertebral bodies (in FIG. 2 the pair of cages 10 are inserted between the fifth lumbar vertebra (L5) and the top of the sacrum (S1). Two cages 10 are generally inserted side by side with the external threading 14 tapping into the lower surface of the vertebral bone above (L5), and the upper surface of the vertebral bone (S1) below. The cages 10 include holes 18 through which the adjacent bones are to grow. Additional material, for example autogenous bone graft materials, may be inserted into the hollow interior 20 of the cage 10 to incite or accelerate the growth of the bone into the cage. End caps (not shown) are often utilized to hold the bone graft material within the cage 10.

These cages of the prior art have enjoyed medical success in promoting fusion and grossly approximating proper disc height. It is, however, important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. It would therefore, be a considerable advance in the art to provide an implant assembly which does not promote fusion, but, rather, which nearly completely mimics the biomechanical action of the natural disc cartilage, thereby permitting continued normal motion and stress distribution. It is, therefore, an object of the present invention to provide a new and novel intervertebral spacer which stabilizes the spine without promoting a bone fusion across the intervertebral space.

It is further an object of the present invention to provide an implant device which stabilizes the spine while still permitting normal motion.

It is further an object of the present invention to provide a device for implantation into the intervertebral space which does not promote the abnormal distribution of biomechanical stresses on the patient's spine.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a flexible intervertebral spacer device comprising a pair of spaced apart base plates, arranged in a substantially parallel planar alignment (or slightly offset relative to one another in accordance with proper lordotic angulation) and coupled to one another by means of a spring mechanism. In particular, this spring mechanism provides a strong restoring force when a compressive load is applied to the plates, and may also permit limited rotation of the two plates relative to one another. While there are a wide variety of embodiments contemplated, two embodiments (and variations of both) are described herein as representative of preferred types. Each of these embodiments includes a spirally slotted and radially varying thickness belleville washer utilized as its restoring force providing element.

More particularly, with respect to the base plates, which are similar in all embodiments, as the assembly is to be positioned between the facing surfaces of adjacent vertebral bodies, and as such need to have substantially flat external surfaces which seat against the opposing bone surfaces. In as much as these bone surfaces are often concave, it is anticipated that the opposing plates may be convex in accordance with the average topology of the spinal anatomy. In addition, the plates are to mate with the bone surfaces in such a way as to not rotate relative thereto. (The plates rotate relative to one another, but not with respect to the bone surfaces to which they are each in contact with.) In order to prevent rotation of a plate relative to the bone, the upper and lower plates may each further include outwardly directed spikes which penetrate the bone surface and mechanically hold the plates in place. It is further anticipated that the plates could include a porous coating into which the bone of the vertebral body can grow, however, it is not a limitation which is required of embodiments of the invention. (Note that this limited fusion of the bone to the base plate does not extend across the intervertebral space.)

While not preferred, it is possible, that between the base plates, on the exterior of the device, there may be included a circumferential wall which is resilient and which simply prevents vessels and tissues from entering within the interior of the device. This resilient wall may comprise a porous fabric or a semi-impermeable elastomeric material. Suitable tissue compatible materials meeting the simple mechanical requirements of flexibility and durability are prevalent in a number of medical fields including cardiovascular medicine, wherein such materials are utilized for venous and arterial wall repair, or for use with artificial valve replacements. Alternatively, suitable plastic materials are utilized in the surgical repair of gross damage to muscles and organs. Still further materials which could be utilized herein may be found in the field of orthopedic in conjunction with ligament and tendon repair. It is anticipated that future developments in this area will produce materials which are compatible for use with this invention, the breadth of which shall not be limited by the choice of such a material. Notwithstanding the foregoing, such an exterior shroud and/or the interior elastomeric materials which may be compatible with the present invention, they are not preferred for use with the present device.

As introduced above, the internal structure of the present invention comprises a spring member, which provides a restoring force when compressed. More particularly, the force restoring member comprises at least one belleville washer. In the embodiments described herein, the belleville washer has a radially varying thickness. It is desirable that the restoring forces be directed outward against the opposing plates, and for the restoring force versus load profile to vary in a manner which approximates that of the normal healthy intervertebral cartilage. In addition, it is desirable that the restoring force providing subassembly not substantially interfere with the rotation of the opposing plates relative to one another, at least through a range of angles equivalent to that permitted by normal healthy intervertebral cartilage.

More particularly, the restoring force providing subassembly comprises a belleville washer having a radially varying thickness. Belleville washers are washers which are generally bowed in the radial direction. Specifically, they have a radial convexity (i.e., the height of the washers is not linearly related to the radial distance, but may, for example, be parabolic in shape). The restoring force of a belleville washer is proportional to the elastic properties and the thickness of the material. In addition, the magnitude of the compressive load support and the restoring force provided by the belleville washer may be modified by providing slots in the washer. In the present invention, there are two separate embodiments each having two variations. The two variations described herein relate to whether the washers include spiral slots which initiate on the periphery of the washer and extend along arcs which are generally radially inwardly directed a distance toward the center of the bowed disc.

The first embodiment (which can exist in two variations, i.e. slotted or unslotted) comprises a radially varying thickness which is grows thicker as the radius increases (the thickness is directly proportional to the radius). In the second embodiment (also existing in the two embodiments which can be either slotted or unslotted), the washers comprise a radially varying thickness which is grows thinner as the radius increases (the thickness is inversely proportional to the radius).

In both of these embodiments, superior reproduction of the anatomical deflection to load characteristics is achieved. As a compressive load is applied to a belleville washer, the forces are directed into a hoop stress which tends to radially expand the washer. This hoop stress is counterbalanced by the material strength of the washer, and the strain of the material causes a deflection in the height of the washer. Stated equivalently, a belleville washer responds to a compressive load by deflecting compressively, but provides a restoring force which is proportional to the elastic modulus of the material in a hoop stressed condition. The purpose of the present invention is to create a non-linear load deflection profile by permitting a portion of the washer to deflect early in the loading, and a more rigid portion to deflect only under more severe loadings. By varying the thickness of the washer material smoothly across it's radial extent, this goal is achieved.

It is preferred that either embodiment be of the variation in which the slots are provided inasmuch as the slots permit the washer to expands and restores itself far more elastically than a solid washer.

In general, the belleville washer is one of the strongest configurations for a spring, and is highly suitable for use as a restoring force providing subassembly for use in an intervertebral spacer element which must endure considerable cyclical loading in an active human adult.

Referring now to the specific structure of the device, the selected belleville washer is utilized in conjunction with a ball-shaped post on which it is free to rotate through a range of angles (thus permitting the plates to rotate relative to one another through a corresponding range of angles). More particularly, the invention comprises a pair of spaced apart base plates, the first of which is simply a disc shaped member having external and internal flat faces. This first plate further includes a circular retaining wall for housing therein a selected belleville washer and a retaining ring. The other of the plates is similarly shaped, having a flat exterior surface, but includes a short central post portion instead of the circular retaining wall. This central post rises out of the interior face at a nearly perpendicular angle. The top of this short post portion includes a ball-shaped knob. The knob includes a central threaded axial bore which receives a small set screw. Prior to the insertion of the set screw, the ball-shaped head of the post can deflect radially inward (so that the ball-shaped knob contracts). The insertion of the set screw eliminates the capacity for this deflection.

As introduced above, radially modified thickness (and potentially spirally slotted) belleville washer is mounted to this ball-shaped knob in such a way that it may rotate freely through a range of angles equivalent to the fraction of normal human spine rotation (to mimic normal disc rotation). The belleville washer of this design is modified by including an enlarged inner circumferential portion (at the center of the washer) which accommodates the ball-shaped portion of the post. More particularly, the enlarged portion of the modified belleville washer includes a curvate volume having a substantially constant radius of curvature which is also substantially equivalent to the radius of the ball-shaped head of the post. The deflectability of the ball-shaped head of the post, prior to the insertion of the set screw, permits the head to be inserted into the interior volume at the center of the belleville washer. Subsequent introduction of the set screw into the axial bore of the post prevents the ball-shaped head from deflecting. Thereby, the washer can be secured to the ball-shaped head so that it can rotate thereon through a range of proper lordotic angles (in some embodiments, a tightening of the set screw locks the washer on the ball-shaped head at one of the lordotic angles). This assembly provides ample spring-like performance with respect to axial compressive loads, as well as long cycle life to mimic the axial biomechanical performance of the normal human intervertebral disc.

BRIEF DESCRIPTION OF THE DRAWINGS

FIGS. 8a, 8b, and 8c are top views of the opposing plates, and more particularly.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope, which scope shall be determined only by the claims appended hereto. Like numbers refer to similar features of like elements throughout.

Figure 3A:
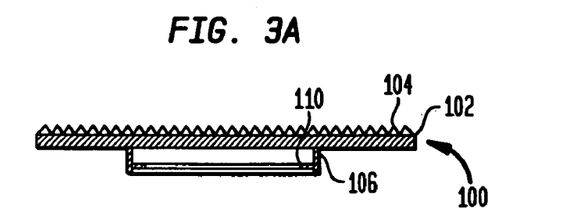
FIGS. 3a and 3b are side cross-section views of the upper and lower opposing plates of the present invention.
Figure 3B:
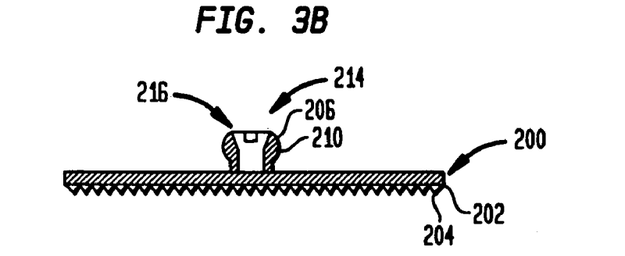

Referring now to FIGS. 3a and 3b, side cross-section views of the top and bottom plate members 100,200 of a first embodiment of the present invention is shown. As the device is designed to be positioned between the facing surfaces of adjacent vertebral bodies, the plates include substantially flat surface portions 102,202 which seat against the opposing bone surfaces. In addition, the plates are to mate with the bone surfaces in such a way as to not rotate relative thereto. It is, therefore, preferred that the plates should include a porous coating 104,204 into which the bone of the vertebral body can grow. (Note that this limited fusion of the bone to the base plate does not extend across the intervertebral space.)

Figure 7:
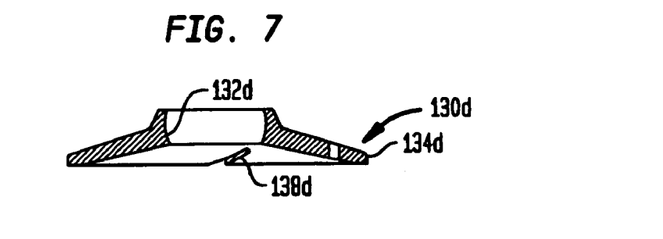
FIG. 7 shows a cross-sectional view of a belleville washer, in accordance with another preferred embodiment of the present invention.
Figure 8A:
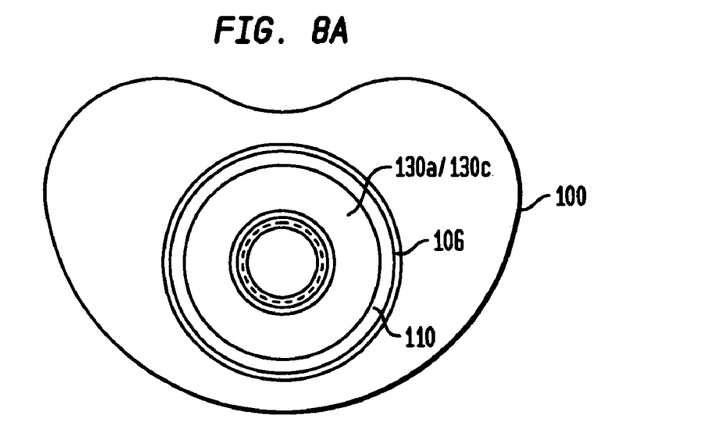
FIG. 8a is a top view of the plate having a post element which seats within the central opening of the belleville washer.
Figure 8B:
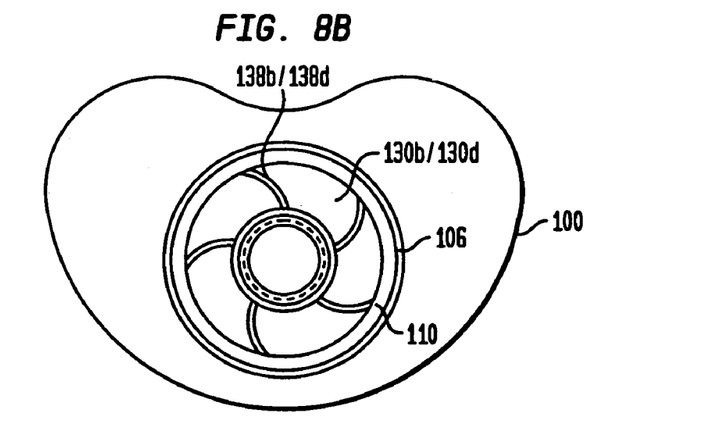
FIG. 8b is a top view of the plate having the circumferential skirt and a retaining ring, in which a belleville washer of the type of FIGS. 4–7 is disposed within the skirt.

Referring now also to FIGS. 8a and 8b, plate 100 further includes a circumferential skirt 106 which serves as a retaining wall, into which the large end of a belleville washer (see FIGS. 4–7) may be seated. The diameter of the retaining wall 106 is preferably slightly wider than the diameter of the undeflected belleville washer such that the loading thereof can result in an unrestrained radial deflection of the washer. The inner surface of the retaining wall 106 includes an annular recess into which a retaining ring may be provided for holding the belleville washer in place (see the assembled FIGS. 9–12).

Figure 8C:
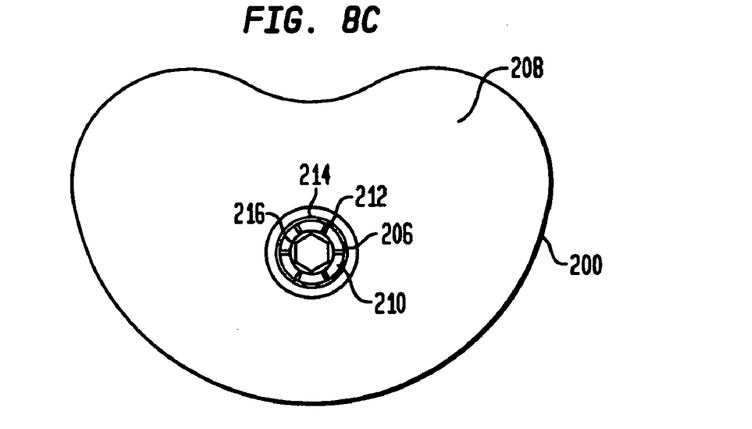
FIG. 8c is a top view of the plate having the circumferential skirt and a retaining ring, in which a belleville washer of the type of FIGS. 4–7 is disposed within the skirt.
Figure 9:
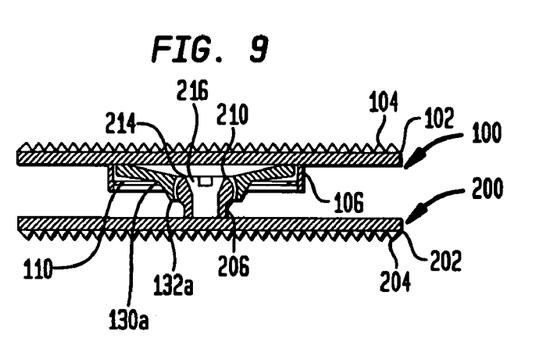
FIGS. 9, 10, 11, and 12 are side cross-section views of various embodiments of the present invention which utilizes the corresponding belleville washers illustrated in FIGS. 4–7 mounted between the plates illustrated in FIGS. 3a and 3b.
Figure 10:
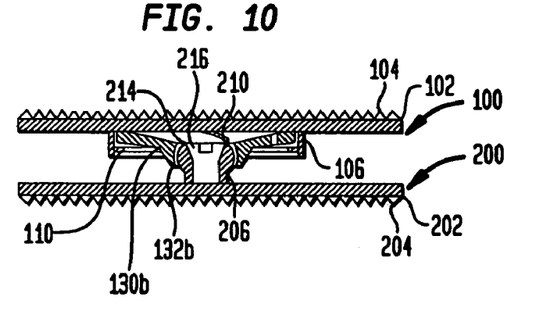
Figure 11:
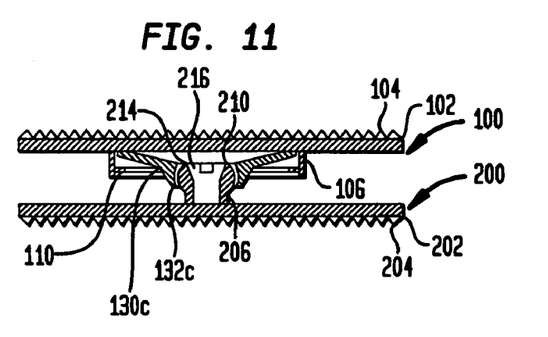
Figure 12:
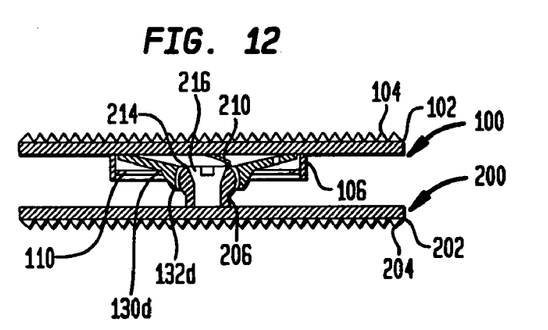

Referring now also to FIG. 8c, plate 200 further includes a central post 206 which rises out of the interior face 208 at a nearly perpendicular angle. The top of this short post member 206 includes a ball-shaped head 210. The head 210 includes a series of slots 212 which render it compressible and expandable in correspondence with a radial pressure (or a radial component of a pressure applied thereto). There is a central threaded axial bore 214 which extends down the post 206. This threaded bore 214 is designed to receive a small set screw 216. Prior to the insertion of the set screw 216, the ball-shaped head 210 can deflect radially inward (so that the ball-shaped head contracts) permitting the belleville washer to be flexibly mounted thereon. The insertion of the set screw 216 eliminates (or greatly reduces) the capacity for this deflection.

Referring now to FIGS. 4–7, side cross-section views of four separate embodiments of the belleville washers are provided. In general, these belleville washers 130 comprise a domed circular shape (a section of a sphere or three dimensional paraboloid would be an appropriately corresponding shape), having a central opening 132 and an outer edge 134. As a compressive load is applied to a belleville washer, the forces are directed into a hoop stress which tends to radially expand the washer. This hoop stress is counter-balanced by the material strength of the washer, and the strain of the material causes a deflection in the height of the washer. Stated equivalently, a belleville washer responds to a compressive load by deflecting compressively, but provides a restoring force which is proportional to the elastic modulus of the material in a hoop stressed condition. In the present invention, the thickness (the distance from the concave surface to the convex surface) of the material which comprises the washer varies from the edge of the central opening 132 to the outer edge 134 of the element.

Figure 4:
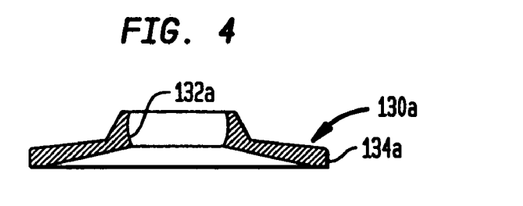
FIG. 4 shows a cross-sectional view of a belleville washer with a thinner inner portion and a thicker outer portion.

More particularly with respect to the washer in FIG. 4 (and shown within the circumferential ring of plate 100 in FIG. 8b), the belleville washer 130a has a greater thickness at the outer edge 134a than at the edge of the central opening. As the restoring force of a belleville washer is proportional to the elastic properties of the material as well as the quantity of material being loaded, the reduction of the material at the edge of the central opening 132a permits a load/deflection profile in which the load which deflects the inner portion of the washer is less than the outer portion. This permits the washer to compress to initially compress easily under a light loading, but to rapidly (faster than a straight linear loading profile) become stiff and resist deflection. This loading profile is more anatomically relevant with respect to mimicking the performance of the cartilage present in a healthy intervertebral space.

Figure 5:
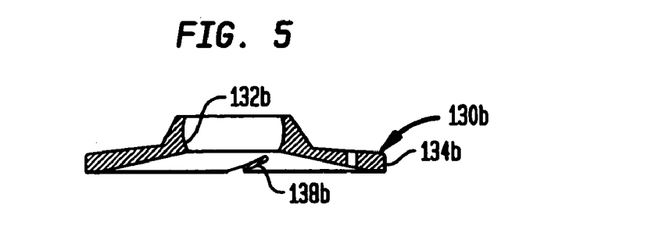
FIG. 5 shows another cross-sectional view of a belleville washer, in accordance with another preferred embodiment of the present invention.

More particularly with respect to the washer in FIG. 5 (and shown within the circumferential ring of plate 100 in FIG. 10), the belleville washer 130b also has a greater thickness at the outer edge 134b than at the edge of the central opening. However, the washer further includes a series of spiral slots 138b extending from the outer edge 134b toward the central opening 132b. The slots 138b extend from the outer diameter of the belleville washer, inward along arcs generally directed toward the central opening 132b of the element. The slots 138b do not extend fully to the center of the device. In preferred embodiments, the slots may extend anywhere from a quarter to three quarters of the overall radius of the washer, depending upon the requirements of the patient, and the anatomical requirements of the device. As the restoring force of a belleville washer is proportional to both the geometry of the material being loaded and its elastic properties, the varying thickness combined with the radial slots 138b permits a load/deflection profile in which the load which deflects the inner portion of the washer is less than the outer portion. This permits the washer to compress to initially compress easily under a light loading, but to rapidly (faster than a straight linear loading profile) become stiff and resist deflection. This loading profile is more anatomically relevant with respect to mimicking the performance of the cartilage present in a healthy intervertebral space.

Figure 6:
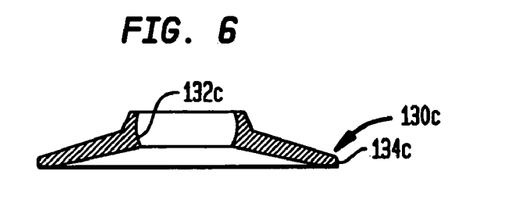
FIG. 6 shows a cross-sectional view of a belleville washer with a thicker inner portion and a thinner outer portion, in accordance with another preferred embodiment of the present invention.

More particularly with respect to the washer in FIG. 6 (and shown within the circumferential ring of plate 100 in FIG. 11), the belleville washer 130c has a smaller thickness at the outer edge 134c than it is at the inner edge 132c. As the restoring force of a belleville washer is proportional to the elastic properties of the material as well as the quantity of material being loaded, the reduction of the material at the outer edge 134c permits a load profile in which the load which deflects the outer portion of the washer is less than the inner portion. This permits the washer to compress to initially compress easily under a light loading (as a result of outer edge deflection), but to rapidly (faster than a straight linear loading profile) become stiff and resist deflection. This loading profile is more anatomically relevant with respect to mimicking the performance of the cartilage present in a healthy intervertebral space.

More particularly with respect to the washer in FIG. 7 (and shown within the circumferential ring of plate 100 in FIG. 12), the belleville washer 130d has a smaller thickness at the outer edge 134d than at the edge of the central opening. However, the washer further includes a series of spiral slots 138d extending from the outer edge 134d toward the central opening. The slots 138d extend from the outer diameter of the belleville washer, inward along arcs generally directed toward the central opening of the element. The slots 138d do not extend fully to the center of the device. In preferred embodiments, the slots may extend anywhere from a quarter to three quarters of the overall radius of the washer, depending upon the requirements of the patient, and the anatomical requirements of the device. As the restoring force of a belleville washer is proportional to both the geometry of the material being loaded and its elastic properties, the varying thickness combined with the radial slots 138d permits a load/deflection profile in which the load which deflects the inner portion of the washer is less than the outer portion. This permits the washer to compress to initially compress easily under a light loading, but to rapidly (faster than a straight linear loading profile) become stiff and resist deflection. This loading profile is more anatomically relevant with respect to mimicking the performance of the cartilage present in a healthy intervertebral space.

In addition, the central openings of each of the belleville washer embodiments described hereinabove further includes a curvate volume for receiving therein the ball-shaped head 210 of the post 206 of the lower plate 200 described above.

Referring now to FIGS. 9–12, side cross-sectional views of the fully assembled embodiments of the intervertebral spacers which comprises the present invention are provided. Each structure includes the belleville washer (selected from the corresponding ones illustrated in FIGS. 4–7). Each further includes the following common features: two opposing plates 100,200 having their flat surfaces 102,202, respectively, directed away from one another (to be seated against the adjacent bone); a retaining ring 110 is seated in the annular groove of the retaining wall 106; and a ball-shaped-headed central post 206 extending into the central opening 132 of the corresponding belleville washer 130, rotatably secured in place by set screw 216. The deflectability of the ball-shaped head of the post 206, prior to the insertion of the set screw 216, permits the head to be inserted into the interior volume at the center of the belleville washer 130. Subsequent introduction of the set screw 216 into the axial bore of the post 206 prevents the ball-shaped head from deflecting. Thereby, the washer 130 can be secured to the ball-shaped head so that it can rotate thereon through a range of proper lordotic angles. While not in this preferred embodiment, it should be noted that in other embodiments, a tightening of the set screw can lock the washer 130 on the ball-shaped head at one of the lordotic angles.

We claim:
1. An intervertebral spacer device comprising:
   first and second plate members, each having first and second plate surfaces thereof, said plate members being disposed in a spaced apart relationship such that said first plate surfaces oppose one another, and said second plate surfaces face in opposite directions; and
   at least one subassembly disposed between said first plate surfaces of said first and second plate members, and disposed such that at least a portion of a compressive load applied to said second plate surfaces of said plate members is transmitted to said at least one subassembly,
   said subassembly including a ball captured in a curvate volume, at least a portion of said curvate volume being formed in a convex element that is maintained against said first plate member by a retaining wall and a retaining ring, the retaining ring being circumferentially adjacent a large end of said convex element, the retaining wall being on the first plate member and engaged with the retaining ring to hold said convex element against said first plate member, wherein said convex element is movable relative to said first plate member after said intervertebral spacer device is fully assembled for insertion into an intervertebral space, said subassembly establishing a center of rotation between said first and second plate members and about which said first and second plate members rotate relative to one another.

2. The device as set forth in claim 1, wherein said subassembly is a restoring force providing subassembly and is disposed between said first plate surfaces such that said portion of said compressive load is counteracted by said restoring force providing subassembly.

3. The device as set forth in claim 2, wherein said restoring force providing subassembly includes said convex element, and said convex element is a belleville washer.

4. The device as set forth in claim 1, wherein said subassembly further includes a post structure extending from said second plate member, and which post structure includes said ball.

5. The device as set forth in claim 4, wherein said post structure further includes a threaded bore that extends axially from said ball toward said second plate member, and which bore receives therein a threaded set screw such that prior to insertion of the set screw therein, said bore permits the ball to compress radially inwardly, and such that after the insertion of said set screw said ball is not readily radially compressible.

6. The device as set forth in claim 1, wherein the retaining wall extends from said first plate surface of said first plate member.

7. The device as set forth in claim 1, wherein the retaining wall is in contact with said first plate surface of said first plate member.

8. The device as set forth in claim 1, wherein the retaining wall and the retaining ring define a space over said first plate surface of said first plate member, and wherein said convex element is movable relative to said first plate surface of said first plate member.

9. The device as set forth in claim 8, wherein the retaining wall and the retaining ring cooperate together for limiting movement of said convex element relative to said first plate member.

* * * * *